(12) United States Patent
McDonnell et al.

(10) Patent No.: US 8,888,862 B2
(45) Date of Patent: Nov. 18, 2014

(54) BONE IMPLANT WITH A SURFACE ANCHORING STRUCTURE

(76) Inventors: Patrick McDonnell, Galway (IE); Noel Harrison, Galway (IE)

( * ) Notice: Subject to any disclaimer, the term of this patent is extended or adjusted under 35 U.S.C. 154(b) by 92 days.

(21) Appl. No.: 12/783,025

(22) Filed: May 19, 2010

(65) Prior Publication Data

US 2010/0298950 A1 Nov. 25, 2010

(30) Foreign Application Priority Data

May 19, 2009 (EP) .................................. 09006746

(51) Int. Cl.
*A61F 2/28* (2006.01)
*A61F 2/30* (2006.01)
*A61F 2/36* (2006.01)
*A61F 2/46* (2006.01)

(52) U.S. Cl.
CPC ........... *A61F 2/30771* (2013.01); *A61F 2/3662* (2013.01); *A61F 2/3094* (2013.01); *A61F 2/36* (2013.01); *A61F 2002/30013* (2013.01); *A61F 2002/30113* (2013.01); *A61F 2002/30156* (2013.01); *A61F 2002/30179* (2013.01); *A61F 2002/30225* (2013.01); *A61F 2002/30322* (2013.01); *A61F 2002/30808* (2013.01);

(Continued)

(58) Field of Classification Search
None
See application file for complete search history.

(56) References Cited

U.S. PATENT DOCUMENTS

| 5,348,788 | A | 9/1994 | White | |
| 5,665,091 | A * | 9/1997 | Noble et al. | 606/85 |
| 6,468,309 | B1 * | 10/2002 | Lieberman | 623/17.11 |
| 7,018,418 | B2 * | 3/2006 | Amrich et al. | 623/23.5 |
| 7,244,275 | B2 * | 7/2007 | Michelson | 623/23.5 |
| 2002/0040242 | A1 * | 4/2002 | Picha et al. | 623/17.11 |
| 2006/0100705 | A1 * | 5/2006 | Puno et al. | 623/17.11 |

(Continued)

FOREIGN PATENT DOCUMENTS

| DE | 101 20 330 A | 11/2002 |
| EP | 0 230 006 A | 7/1987 |

(Continued)

OTHER PUBLICATIONS

Extended European Search Report from priority application EP 09006746.3 dated Oct. 23, 2009.

*Primary Examiner* — Thomas J Sweet
*Assistant Examiner* — Rebecca Preston (57) ABSTRACT

A bone implant comprises a core 10 having an integral anchoring structure 12 at its surface. The structure 12 comprises an array of upwardly extending mutually spaced pointed claw-like teeth 14 for digging into bone to which the implant is to be attached, and a network of pores 16 underlying the array and communicating with the exterior of the surface via openings 18 between the teeth, the pores allowing for the circulation of nutrients to promote bone growth.

11 Claims, 8 Drawing Sheets

(52) U.S. Cl.
CPC ............... *A61F 2002/30812* (2013.01); *A61F 2002/30841* (2013.01); *A61F 2002/30892* (2013.01); *A61F 2002/30909* (2013.01); *A61F 2002/3092* (2013.01); *A61F 2002/30952* (2013.01); *A61F 2002/30968* (2013.01); *A61F 2002/3097* (2013.01); *A61F 2002/3611* (2013.01); *A61F 2002/3625* (2013.01); *A61F 2002/3631* (2013.01); *A61F 2002/4681* (2013.01); *A61F 2230/0006* (2013.01); *A61F 2230/0023* (2013.01); *A61F 2230/0058* (2013.01); *A61F 2230/0069* (2013.01); *A61F 2250/0024* (2013.01); *A61F 2250/0026* (2013.01); *A61F 2310/00011* (2013.01); *A61F 2310/00023* (2013.01); *A61F 2310/00029* (2013.01)
USPC ............... 623/23.5; 623/23.55; 623/23.26; 623/23.3

(56) References Cited

U.S. PATENT DOCUMENTS

| | | | |
|---|---|---|---|
| 2006/0105295 A1* | 5/2006 | Mayer et al. | 433/173 |
| 2006/0235518 A1* | 10/2006 | Blain | 623/17.11 |
| 2008/0195103 A1* | 8/2008 | Lawis et al. | 606/80 |
| 2008/0200957 A1 | 8/2008 | Marcacci | |

FOREIGN PATENT DOCUMENTS

| | | |
|---|---|---|
| EP | 0 420 542 A | 4/1991 |
| WO | 97/36708 A | 10/1997 |
| WO | 97/38649 A | 10/1997 |
| WO | 2006/125711 A | 11/2006 |
| WO | 2007/113862 A | 10/2007 |

* cited by examiner

BONE IMPLANT WITH A SURFACE ANCHORING STRUCTURE

This invention relates to a bone implant having a surface structure for anchoring the implant to a bone without the use of cement.

Primary fixation refers to the fixation of an implant during the initial period after insertion by the surgeon (first few weeks). During this period it is desirable that micromotions of the implant relative to the host bone are minimised so that growth of hard bone tissue into the pores of the implant is promoted. If there is excessive micromotion, then fibrous tissue tends to develop instead of hard bone resulting in poor fixation of the implant [Engh et al., Clinical Orthopaedics and Related Research, 1992].

Secondary fixation refers to the long-term fixation of the implant, following the initial primary fixation period. During this period, it is desirable for hard bone to grow into the pores of the implant and firmly fix it in place relative to the host bone. If there is poor primary fixation, then it will not be possible to achieve good secondary fixation [Abdul-Kadir et al., J. Biomechanics, 2008].

Current commercially available cementless implants incorporate a variety of surface features to encourage bone in-growth, including spherical beads, meshes and roughened surfaces. The most commonly used surface coating consists of a plasma sprayed porous coating of metal beads. However, the architecture of this type of porous surface cannot be optimised and studies of failed implants which have been removed from patients, have raised questions about the effectiveness of bone in-growth into the implant surface [Cook et al., J. Bone Joint Surg, 1991, Engh et al., J. Bone Joint Surg, 1995]. Also, the coating must be applied to the core in a separate manufacturing step, resulting in increased cost and the risk of debonding from the core [Hollister, Current Orthopaedics, 1995, Hamilton et al., J. Arthroplasty, 2007].

U.S. Pat. No. 7,018,418 describes a textured surface for medical implants having micro recesses such that the outer surface overhangs the micro recesses. Embodiments of the textured surface include sharp edges for promoting bone deposition and growth within the micro recesses, protrusions of varying depth from the surface that include overhangs, and micro recesses that are at least partially defined by complex ellipsoids.

U.S. Pat. No. 4,272,855 describes an anchoring surface of a bone implant provided with villi (depressions or projections) devoid of corners and edges. The villi are of generally conical shape with transition surfaces merging into the base level of the anchoring surface. The villi allow implanting in a bone without cement since bone tissue is allowed to grow into or around the villi.

US2007/0142914 describes a method of forming an implant having a porous tissue ingrowth structure and a bearing support structure. The method includes depositing a first layer of a metal powder onto a substrate, scanning a laser beam over the powder so as to sinter the metal powder at predetermined locations, depositing at least one layer of the metal powder onto the first layer and repeating the scanning of the laser beam.

Further examples of the prior art can be found in EP 0760687; US 2008/0288083; EP 0420542; US 2004/0191106; and US 2006/0147332.

It is an object of the invention to provide an improved bone implant which facilitates both primary and secondary fixation.

According to the present invention there is provided a bone implant comprising a stem having an integral anchoring structure at its surface, the structure comprising an array of mutually spaced pointed teeth formed along at least a portion of the length of the stem, each tooth forming an overhang generally in the form of a claw for digging into bone to which the stem is to be attached, and a network of pores underlying the array and communicating with the exterior of the surface via openings between the teeth, the pores allowing for the circulation of nutrients to promote bone growth.

The structure of the device provides for both primary and secondary fixation of the implant.

Preferably, the openings between the teeth allow growth of bone into the network of pores.

Preferably, the pointed teeth extend upwardly from said core. Preferably, the network of pores are substantially fully interconnected.

In the present context "upwardly" means in a direction generally away from the underlying implant core, and "substantially fully interconnected" means that there is a continuous pathway between substantially every pore in the structure. As the pores are interconnected, this allows for free movement of the appropriate cells and nutrients to promote bone in-growth.

The implant may be manufactured from any suitable material (for example titanium, titanium alloys, cobalt-chromium or other biocompatible metallic material), in a rapid prototyping process using, for example, selective laser sintering, which integrates the surface structure with the solid core.

Embodiments of the invention will now be described, by way of example, with reference to the accompanying drawings, in which.

Although the drawings in FIGS. 1-10 show the anchoring structure as a flat, circular disc, it will be understood that in a practical implementation the structure will be shaped and dimensioned to conform to the contours of a particular bone implant to which it is applied. Also, in FIGS. 1 to 10, only the outermost layer of the implant's core is shown.

Referring to FIGS. 1 to 4, a cementless bone implant comprises a solid core 10 having an integral anchoring structure 12 at its surface. The anchoring structure 12 comprises a two dimensional array of upwardly extending mutually spaced pointed teeth 14 for digging into bone to which the implant is to be attached, and a substantially fully interconnected network of pores 16 underlying the array and communicating with the exterior of the surface via openings 18 between the teeth 14. The anchoring structure 12 is built up integrally with the core 10 by a rapid prototyping process such as direct metal laser sintering (DMLS) or electron beam melting. The anchoring structure and core are made of titanium, titanium alloy, cobalt-chromium or other biocompatible metal material.

Figure 1:
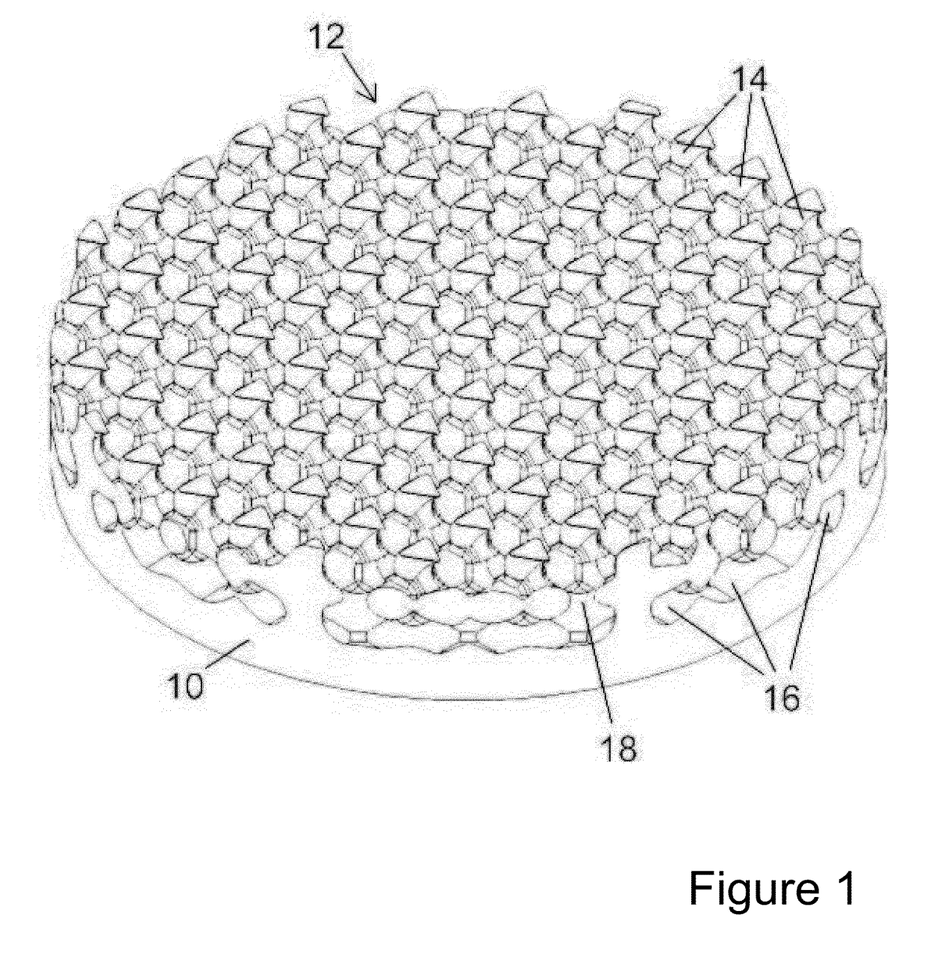
FIG. 1 is a perspective view of a representative part of an anchoring structure at the surface of a bone implant.
Figure 2:
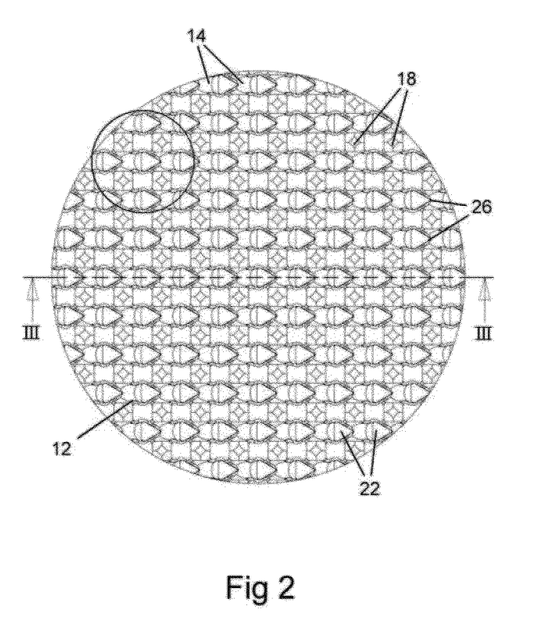
FIG. 2 is a plan view of the anchoring structure of FIG. 1.
Figure 3:
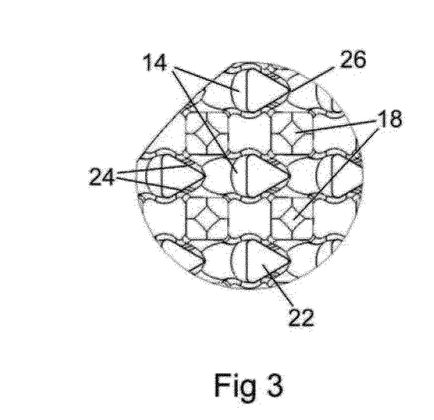
FIG. 3 is an enlarged view of the part of the anchoring structure of FIG. 1 circled in FIG. 2.
Figure 4:
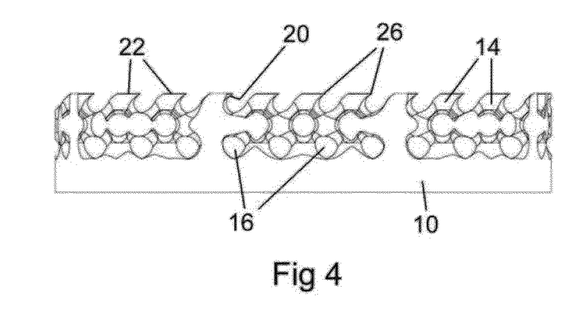
FIG. 4 is a cross-sectional view of the anchoring structure of FIG. 1, taken on the line III-III of FIG. 2.

In the embodiment shown in FIGS. 1 to 4 each tooth 14 forms an overhang 20, FIG. 4, so that it is generally in the form of a claw. Each claw 14 has a substantially triangular upper surface 22 with convergent edges 24 defining a point 26 at the free end of the claw. In the present embodiment the upper surface 22 is substantially parallel to the underlying core 10, but, as will be described, the upper surface 22 may be inclined upwardly to the point 26. In other embodiments the teeth 14 may extend directly upwards without any overhang 20 and terminate in a point. It will also be understood that the anchoring structure 12 may comprise alternative claw shapes, for example a wedge-shaped claw.

Over substantial areas of the implant the claws 14 have a common orientation; for example, in the representative part of the implant shown in FIG. 2, all the claws point towards the right. However, dependent on the design of the particular implant, different areas of the structure may have the claws 14 pointing in different directions respectively. This is to allow the most advantageous attachment to the bone in different areas of the implant. It will be understood that the repeating pattern of the claws may be varied to give optimum primary fixation of the implant to the host bone.

Figure 5A:
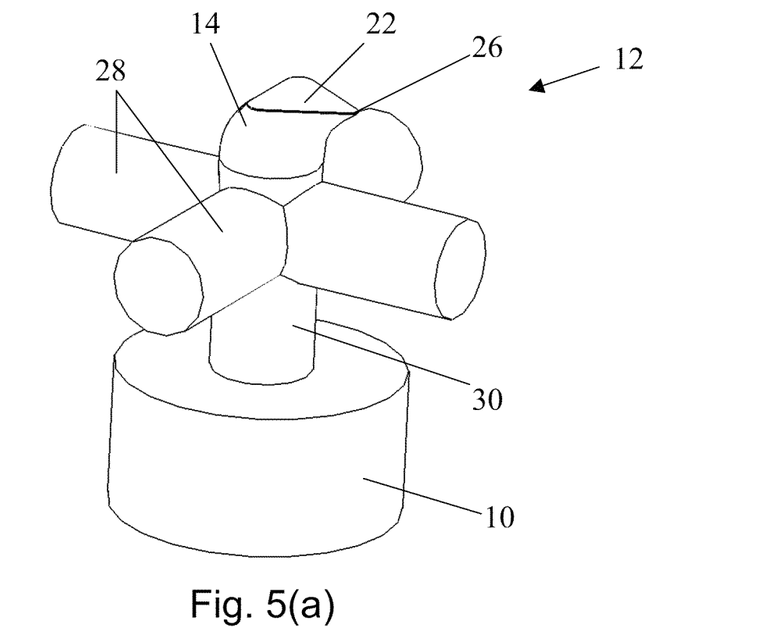
FIGS. 5(a) and (b) show the basic structure underlying the anchoring structure of FIG. 1.
Figure 5B:
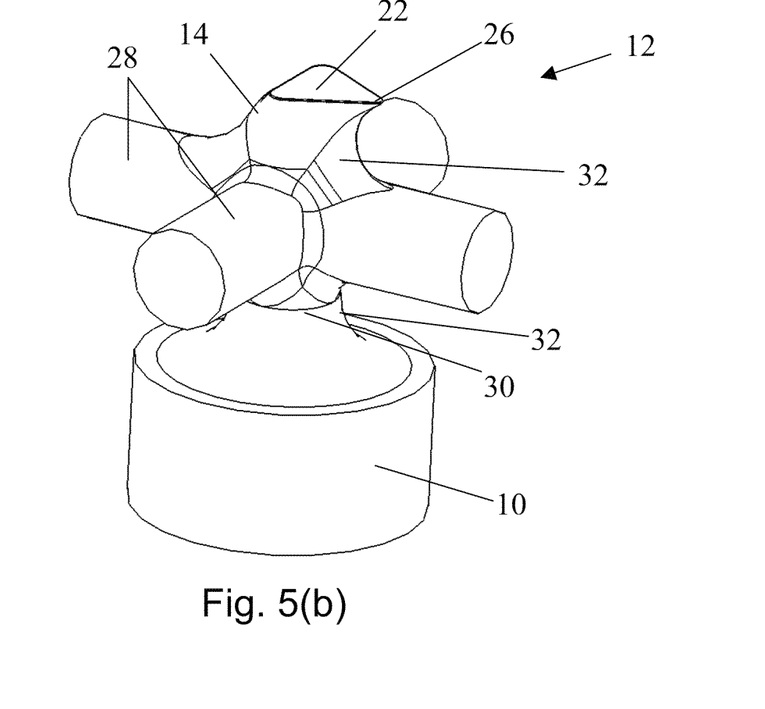

As shown in FIG. 5(a), the structure 12 is actually constructed as a grid of intersecting struts 28 supported above the core 10 by a plurality of pillars 30 intersecting the grid at the intersections of the struts and extending upwardly beyond the strut intersection to form the claws 14. As can be seen in FIG. 5(b), the junctions between the intersecting struts and pillars, and between the pillars and underlying core, are filleted as indicated schematically by the dashed lines 32. It should be understood that the fillets 32 are not applied subsequent to the manufacture of the grid 28 and columns 30, but are formed integrally during the manufacture by, for example, selective laser sintering.

It will be understood that the fillets have been designed to reduce stress concentrations in order to withstand the extreme case loading and fatigue loading conditions that are experienced in-vivo. It will be also be understood that there may be more than one layer in depth of interconnecting struts, i.e. that there could be a 3D lattice of interconnecting struts and pillars, between the outer surface of the implant base 10 and the claws 14.

Figure 6:
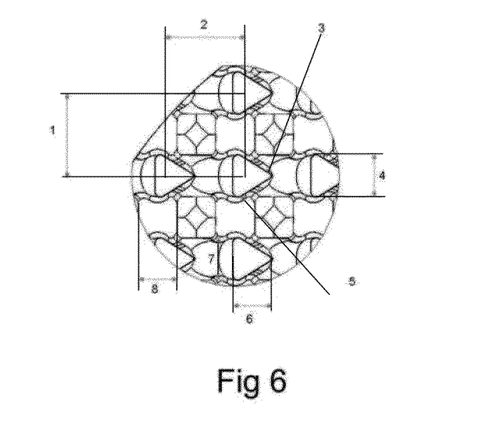
FIGS. 6 and 7 identify certain dimensions of the anchoring structure of FIGS. 1 to 5.
Figure 7:
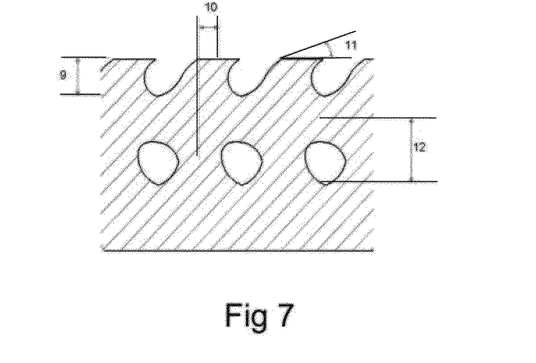

FIGS. 6 and 7 are views similar to FIGS. 3 and 4 in which certain dimensions of the structure 12, listed in the first column of the following table, are indicated by the numerals 1 to 12:

| Structure Dimension | Embodiment (mm) | Preferred Range (mm) |
| --- | --- | --- |
| 1 | 1.4 | 0.7-3.0 |
| 2 | 1.4 | 0.7-3.0 |
| 3 (radius) | 0.04 | 0-0.2 |
| 4 | 0.7 | 0.1-3.0 |
| 5 (radius) | 0.09 | 0-3.0 |
| 6 | 0.64 | 0.1-3.0 |
| 7 | 0.61 | 0.1-3.0 |
| 8 | 0.7 | 0.1-3.0 |
| 9 | 0.5 | 0.1-2.0 |
| 10 | 0.25 | 0-2.0 |
| 11 (°) | 0 | 0-90 |
| 12 | 1.05 | 0.1-3.0 |

The second column lists the values of these dimensions for the particular embodiment of FIGS. 1 to 5, while the third column lists the preferred ranges for these dimensions for all embodiments.

In the above table, dimension (10) gives the offset of the upper surface of the claw, i.e. the distance between the centre line of the pillar and the centre of the top surface of the claw, and dimension (12) gives the distance from the surface of the core to the centreline of the intersecting struts. The radius of the intersecting struts are given in dimensions (4) and (8).

Figure 8:
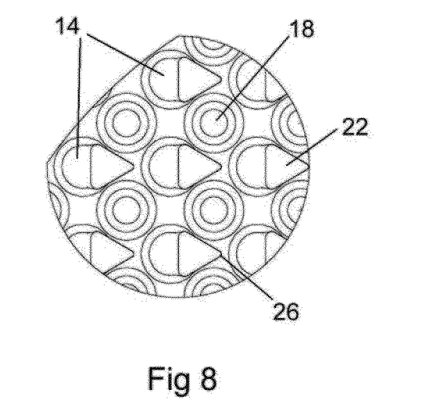
FIGS. 8 and 9 show a second embodiment of the invention in which the upper surface of the claw is at an oblique angle to the surface of the implant base to promote embedding in the host bone.
Figure 9:
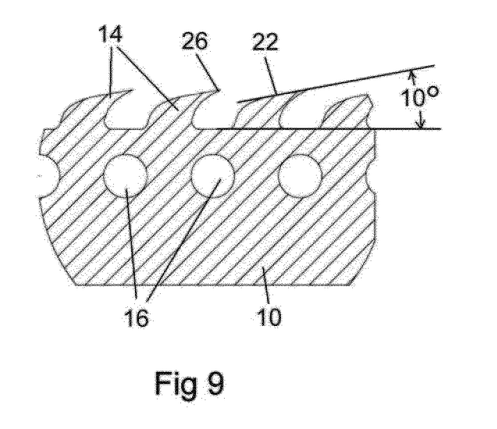

In the foregoing embodiment the angle 11 was 0 degrees. In a second preferred embodiment the angle 11 is 10 degrees, as shown in FIGS. 8 and 9 which are views similar to FIGS. 3 and 4 respectively.

Figure 10:
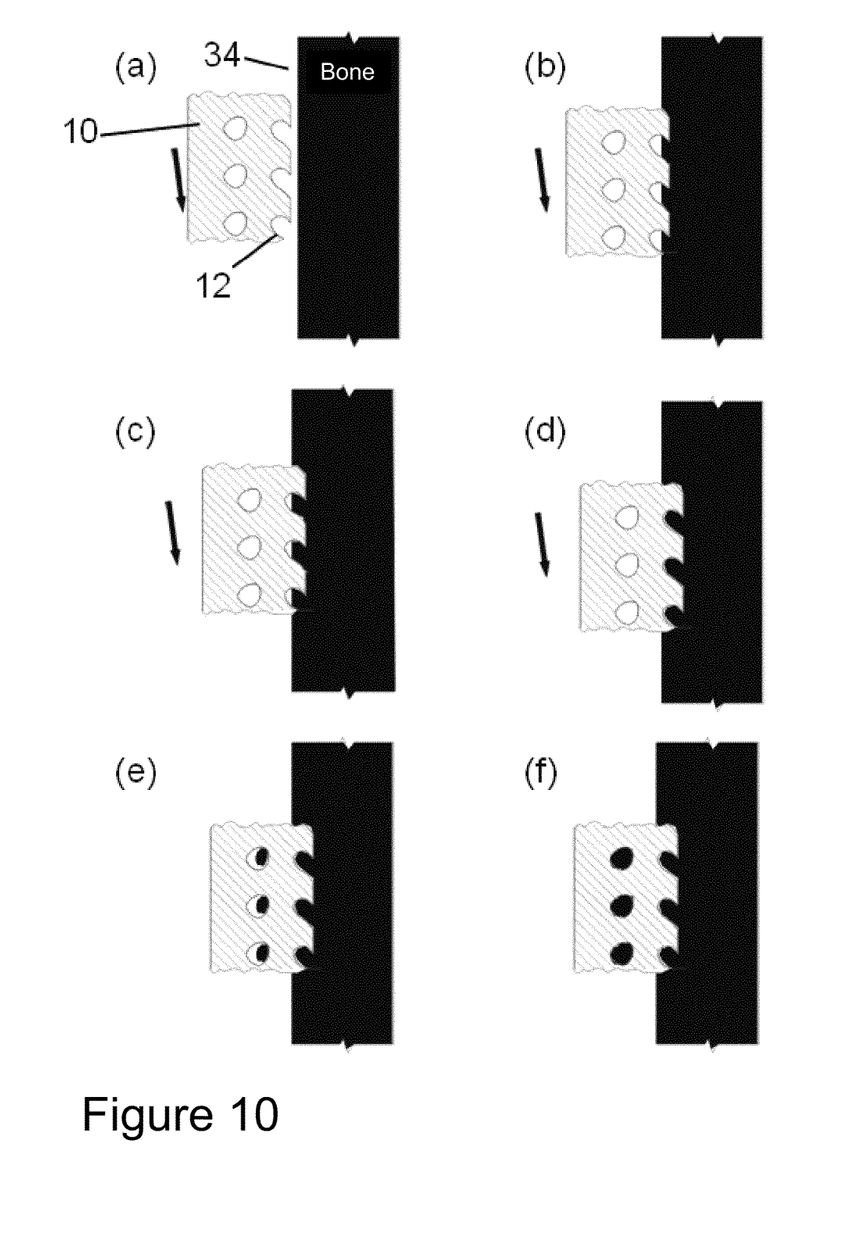
FIG. 10 illustrates the use of the anchoring structure of FIGS. 1 to 5.

FIG. 10 illustrates the successive steps in attaching the implant to a patient's bone 34. Initially, step (a), the implant is pushed onto the bone in the direction indicated by the arrow, and then hammered in place by the surgeon, steps (b) to (d), so that the claws 14 dig into the bone 34. This is the primary fixation, and no cement need be used (although the additional use of cement is not ruled out). The claws are designed to prevent micromotions of the implant during the primary fixation period to avoid the development of fibrous tissue. Steps (e) and (f) show the gradual long term bone growth into the wells between claws 14 and into the network of pores. This is the secondary fixation.

Figure 11A:
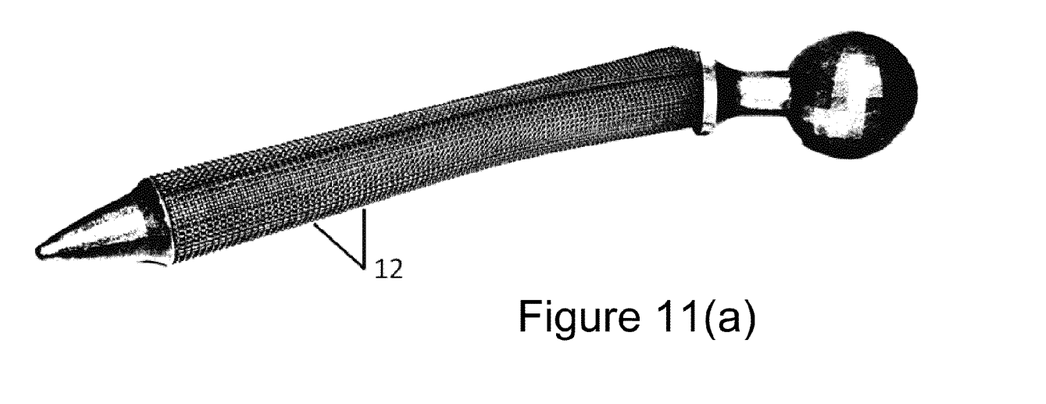
FIG. 11 shows a CAD model and images of a hip replacement stem embodying the invention.
Figure 11B:
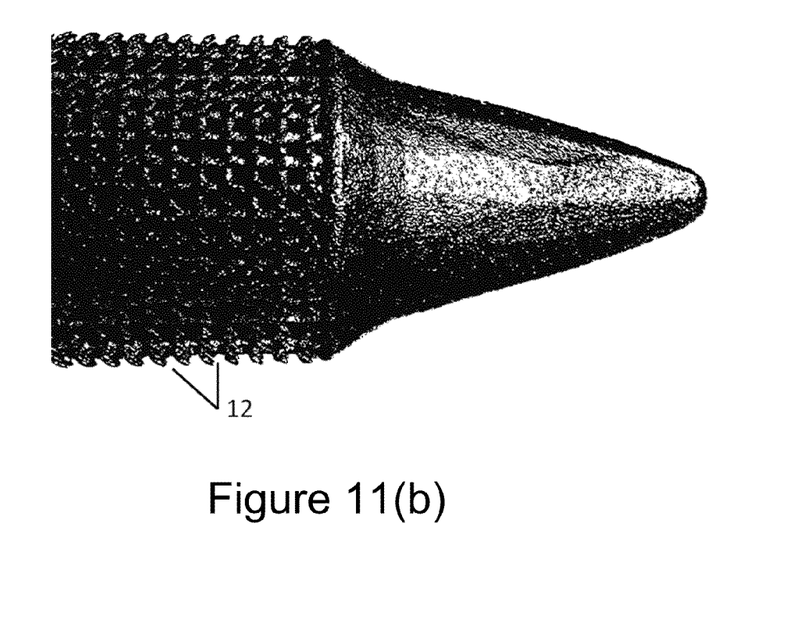

FIG. 11 shows a total hip replacement stem (THRS) embodying the invention. FIG. 11(a) shows a CAD model (A) of the stem. FIG. 11(b) shows an enlarged view of the anchoring structure architecture adjacent the distal end of the implant stem. As seen, the anchoring structure 12 is formed substantially the entire length of the stem body except for the ball joint. It will also be understood that the anchoring structure may be provided on a portion of the stem of the implant.

The THRS incorporates the novel surface anchoring structure 12 described above, designed to encourage bone growth into the stem and to resist in-vivo mechanical loading conditions. The stem is manufactured from titanium in a 1-step rapid prototyping (RP) process which integrates the surface architecture with the solid core. The anchoring structure includes the network of interconnected pores 16 whose dimensions are chosen to give the maximum potential for bone in-growth. The pore junctions are filleted in order to reduce the stresses developed under in-vivo loading conditions. Initial cell culture tests, where bone-type cells were seeded onto coupons with the surface architecture and coupons from commercially available stems, showed that cell proliferation occurs in the new surface architecture, indicating the potential of the new design to provide better bone in-growth compared to existing products on the market. This may result in an increased operational lifetime of the THRS in-vivo, a reduction in required revision operations and, consequently, a marked improvement in patient well-being.

The THRS anchoring structure also includes the claw-like teeth 14 on the external surface of the interconnected pore network which is designed to provide improved primary fixation of the stem immediately after implantation. Primary fixation has been shown to be critical for achieving in-growth of hard bone tissue, since micro-motions of the stem relative to the femur after implantation tend to result in undesirable fibrous tissue instead of hard bone.

The invention is not limited to the embodiments described herein which may be modified or varied without departing from the scope of the invention.

The invention claimed is:

1. A permanent bone implant comprising a stem extending between a proximal end and a distal end, the stem having an integral anchoring structure at a surface of the stem, wherein said distal end has a smaller cross section than said proximal end, the structure comprising an array of mutually spaced pointed teeth formed along at least a portion of the length of the stem, each tooth forming an overhang generally in the form of a claw having an upper surface with convergent edges defining a point of the tooth extending towards said distal end and for digging into a bone in a direction in which the stem is to be attached, and a network of pores underlying the array and communicating with an exterior of the surface via openings between the teeth, the network of pores allowing for circulation of nutrients to promote bone growth, wherein the structure comprises a grid of intersecting struts supported above a core of the implant by a plurality of pillars, each pillar intersecting the grid at respective intersections of the struts and extending upwardly beyond the strut intersection to form the teeth.

2. A bone implant as claimed in claim 1, wherein the openings between the teeth allow growth of bone into the network of pores.

3. A bone implant as claimed in claim 1, wherein the network of pores are substantially fully interconnected.

4. A bone implant as claimed in claim 1, wherein the claws have a common orientation over at least a substantial area of the structure.

5. A bone implant as claimed in claim 4, wherein an upper surface portion of each claw is inclined upwardly to the point of the tooth.

6. A bone implant as claimed in claim 4, wherein an upper surface portion of each claw is substantially parallel to the core of the implant.

7. A bone implant as claimed in claim 1, wherein each claw has a substantially triangular upper surface.

8. A bone implant as claimed in claim 1, wherein junctions between the intersecting struts and pillars, and between the pillars and underlying core, are filleted.

9. A bone implant as claimed in claim 1, wherein the structure is made integral with the core of the implant by a rapid prototyping process such as direct metal laser sintering or electron beam melting.

10. A bone implant as claimed in claim 1, wherein the anchoring structure and the core of the implant are made of titanium, titanium alloy, cobalt chromium or other biocompatible metal material.

11. A bone implant as claimed in claim 1, wherein said proximal end comprises a component of an articulated joint.

* * * * *